United States Patent [19]

Eberle et al.

[11] Patent Number: 4,668,836
[45] Date of Patent: May 26, 1987

[54] PROCESS FOR PRODUCING CYCLOALKADIENES

[75] Inventors: Hans-Jürgen Eberle, Munich; Franz-Heinrich Kreuzer, Martinsried; Norbert Zeitler, Munich, all of Fed. Rep. of Germany

[73] Assignee: Consortium fur Elektrochemische Industrie GmbH, Munich, Fed. Rep. of Germany

[21] Appl. No.: 790,953

[22] Filed: Oct. 24, 1985

[30] Foreign Application Priority Data

Nov. 20, 1984 [DE] Fed. Rep. of Germany ....... 3442376
Jul. 12, 1985 [DE] Fed. Rep. of Germany ....... 3524977

[51] Int. Cl.$^4$ ................................................ C07C 2/42
[52] U.S. Cl. ..................................... 585/364; 585/362; 585/374
[58] Field of Search ............... 585/364, 362, 365, 374, 585/646, 647

[56] References Cited

U.S. PATENT DOCUMENTS 3,728,414  4/1973  Holden et al. ....................... 585/646
3,888,940  6/1975  Kubicek ............................. 585/364

FOREIGN PATENT DOCUMENTS 1105565  3/1968  United Kingdom ................ 585/364

OTHER PUBLICATIONS

Chemiker Zeitung 99, 397–413 (1975), p. 404, 3rd paragraph.

Primary Examiner—Asok Pal
Attorney, Agent, or Firm—Collard, Roe & Galgano

[57] ABSTRACT

A process for producing cycloalkadienes in liquid phase by metathesis reaction of cycloalkenes in the presence of a carrier catalyst based on $Re_2O_7/Al_2O_3$. The cycloalkenes in the form of 0.01 to 0.05 molar solutions are contacted with the carrier catalyst in a fixed bed arrangement with contact times of 10 to 100 seconds.

8 Claims, No Drawings

PROCESS FOR PRODUCING CYCLOALKADIENES

BACKGROUND OF THE INVENTION

The invention relates to a process for producing cycloalkadienes in liquid phase by metathesis reaction of cycloalkenes in the presence of a carrier catalyst based on $Re_2O_7/Al_2O_3$.

From GB-PS 1 105 565, the production of cyclohexadekadiene by methathesis reaction of cyclooctene on an $Re_2O_7/Al_2O_3$-contact is known. Preferably, this known process is carried out as a type of solids extraction in a Soxhlet apparatus. The yield is stated to come to 6% based on the amount of cyclooctene used. The type of reaction on which this process is based can be described as a dimerization of the initial product. The unsatisfactory yield can be ascribed, last but not least, to the fact that the reaction takes place with insufficient selectivity with respect to the dimerization, and also to the formation of a large proportion of higher oligomers.

It has been discovered that in the metathesis reaction of cycloalkenes, the stage of dimerization, (or, if different initial products are used, a stage conforming or equivalent to dimerization) is exceeded to a much lesser degree if the process is carried out with highly diluted solutions of the initial products.

Accordingly, it is an object of the invention to provide a novel process for producing cycloalkadienes in liquid phase by metathesis reaction of cycloalkenes in the presence of a carrier catalyst based on $Re_2O_7/Al_2O_3$.

SUMMARY OF THE INVENTION

Certain of the foregoing and related objects are readily attained according to the invention in a process which includes contacting cycloalkenes with the carrier catalyst in the form of 0.01 to 0.05 molar solutions, with contact or residence periods of from 10 to 100 seconds. The process is particularly tailored for the production of cyclotetradekadiene-1,8 and cyclohexadekadiene-1,9, by means of dimerizing cycloheptene and cyclooctene, respectively. The invention is also particularly well suited for the production of cyclopentadekadiene-1,8 and cycloheptadekadiene-1-6, which can be obtained by metathesis of cycloheptene and cyclooctene, or cyclopentene and cyclododecene, respectively. In particular, carrier catalysts which have $\gamma$-$Al_2O_3$ as the carrier material are used. The specific surface area of the carrier material is expediently in the range of 100 to 300 $m^2/g$ according to BET. The carrier material used is particularly in the form of hollow strands, spheres, cylinders, cubes, cones, and the like. The weight proportion of $Re_2O_7$ to the total weight of the catalyst is preferably from 3 to 20% by weight and, in particular from 3 to 7% by weight. Within the scope of the invention, carrier catalysts based on $Re_2O_7/\gamma$-$Al_2O_3$, which are additionally loaded with tin tetraalkyl as co-catalyst, are preferably used. The amount of the co-catalyst is apportioned in a way such that the molar ratio of $Re_2O_7$ to co-catalyst comes to 5:1 to 1:1. Examples of co-catalysts include tin tetramethyl, tin tetraethyl, tin tetra-n-butyl and others.

The preparation of the carrier catalysts to be used according to the invention is known per se. These catalysts are produced, for example, by impregnating the carrier material with an aqueous solution of ammonium perrhenate, and with subsequent thermal treatment of the product, converting the rhenium compound into the oxide.

In practice, the $Re_2O_7/\gamma$-$Al_2O_3$-contact is loaded with the co-catalyst by treating the catalyst material with solutions of the respective tin tetraalkyls in aliphatic or aromatic hydrocarbons. Examples of such solvents are metathesis-inert solvents used also for diluting the initial substances, namely pentane, hexane, heptane, cyclopentane, cyclohexane, petroleum ether, methylene chloride, chloroform, carbon tetrachloride, chlorobenzene, and m-dichlorobenzene and others.

The cycloolefins to be subjected to metathesis reaction according to the invention are used as 0.01 to 0.05, preferably 0.01 to 0.03 molar solutions in metathesis-inert solvents. In the event of co-metathesis, different cycloalkenes are used as initial substances, and the concentrations relate to the sum of the initial substances. In this case, the initial substances are used with a molar ratio of about 1:1. Examples of metathesis-inert solvents are, in particular, pentane, hexane, heptane, cyclopentane, cyclohexane, methylene chloride, chloroform, carbon tetrachloride, and petroleum ether with a boiling range of 30° to 60° C.

According to the invention, the process is carried out in a fixed bed arrangement, wherein dissolved cycloalkene is passed through the catalyst bed as the liquid phase, and the rate of flow is adjusted in such a way that dwell or contact periods of from 10 to 100 seconds are maintained. As a rule, the reaction temperatures are in the range of 0°–50° C.

By way of example, for carrying out the process a solution of cycloalkene is passed through a vertically mounted tubular reactor filled from top to bottom with catalyst. The reaction mixture discharged from the reactor is loaded into a distilling device and separated into its components. The desired end product is obtained as a relatively high-boiling point fraction. In practical applications, the process is carried continuously in most cases, and the solvent is collected as a low-boiling point substance. Unreacted initial product, if any, is recycled into the reactor after it is charged with fresh initial product.

According to the process of the invention it is possible to produce macrocyclic alkadienes with 14 to 17 carbon atoms, with good yields. The selectivity of the reaction comes to 35 to 50% based on the amount of cycloalkene used. In this way, compounds which, per se, are not readily accessible chemically can be produced in an economical manner. The products of the process are useful in particular in the field of fragrances, for example as starting compounds in the manufacture of musk fragrances.

The invention will now be explained more fully in a number of examples which are, however, only given by way of illustration and not of limitation.

EXAMPLE 1

Preparation of cyclohexadecadiene-1,9

A tubular reactor (length 70 cm, diameter 8 cm) loaded with 1.8 kg of carrier catalyst was used in a vertical arrangement. The reactor catalyst contained 3.5% by weight $Re_2O_7$ and 1.3% by weight tin tetramethyl. The carrier material was $\gamma$-aluminum oxide shaped in the form of hollow strands, with a specific surface of 190 $m^2/g$. A 0.018 molar solution of cyclooctene in n-pentane was passed through the catalyst bed.

The residence time of the mixture was 60 seconds. The temperature in the catalyst bed was adjusted to 15° C.

The reaction mixture discharged from the reactor was passed into a distilling apparatus, wherein n-pentane was distilled off and, after loading with fresh cyclooctene, recycled into the reactor.

The distillative fractionation finally came to a yield of 33.5% of the theoretical yield, based on cyclooctene, and cyclohexadekadiene-1,9 used. The selectivity of the reaction was 37%.

EXAMPLE 2

Preparation of cyclopentadekadiene-1,8

The procedure described in Example 1 was repeated except that instead of using a 0.018 molar solution of cyclooctene in n-pentane, a cyclooctene/cycloheptene mixture was used with a molar ratio of 1:1.1 in n-pentane. The total cycloalkene concentration came to 0.019 moles/L. A residence time of the mixture in the catalyst bed of 70 seconds was maintained.

The distillative fractionation of the reaction mixture produced the following yields:

10.5% cyclotetradekadiene-1,8
10.9% cyclopentadekadiene-1,8, and
15.3% cyclohexadekadiene-1,9.

Thus, while only several embodiments of the present invention have been described, it will be obvious that many changes and modifications may be made thereunto, without departing from the spirit and scope of the invention.

What is claimed is:

1. In a process for producing a cycloalkadiene in liquid phase including the step of performing a metathesis reaction of cycloalkene in the presence of a carrier catalyst comprising $Re_2O_7/Al_2O_3$, the improvement comprising the steps of:

contacting said cycloalkene in the form of 0.01 to 0.05 molar solution with said carrier catalyst for a contact period of 10 to 100 seconds.

2. The process as described in claim 1 wherein the weight proportion of $Re_2O_7$ in the total weight of the catalyst is from 3–20% by weight.

3. The process as described in claim 1 wherein the reaction occurs additionally in the presence of a co-catalyst.

4. The process as described in claim 1 wherein the catalyst is in a fixed bed arrangement.

5. The process as described in claim 3 wherein the co-catalyst is a member selected from the group consisting of tin tetraalkyls, tin tetramethyl, tin tetraethyl and tin tetra-n-butyl.

6. The process as described in claim 1 wherein the carrier material is aluminum oxide.

7. The process as described in claim 1, wherein the reaction temperature is in the range of 0°–50° C.

8. The process as described in claim 1, wherein the carrier material has a BET surface area in the range of 100 to 300 $m^2/g$.

* * * * *